United States Patent [19]
Luisi

[11] Patent Number: 5,294,249
[45] Date of Patent: Mar. 15, 1994

[54] BLENDPOLYMERS

[76] Inventor: Pier L. Luisi, Institut für Polymere, ETH Zentrum, CH 8092 Zürich, Switzerland

[21] Appl. No.: 974,337

[22] Filed: Nov. 10, 1992

Related U.S. Application Data

[63] Continuation of Ser. No. 710,556, Jun. 5, 1991, abandoned, which is a continuation of Ser. No. 286,950, Jan. 13, 1989, abandoned.

[30] Foreign Application Priority Data

Mar. 27, 1987 [CH] Switzerland ............ 1173/87-2

[51] Int. Cl.$^5$ ............ C08L 3/04; C08L 89/00
[52] U.S. Cl. ............ 106/130; 530/411
[58] Field of Search ............ 106/130; 530/411

[56] References Cited

U.S. PATENT DOCUMENTS

| | | | |
|---|---|---|---|
| 809,068 | 1/1906 | Lichtenstein | 106/130 |
| 864,388 | 8/1907 | Schwarzborg et al. | 106/130 |
| 1,911,400 | 5/1933 | Schulte | 106/130 |
| 2,086,032 | 7/1937 | Hoskins | 106/130 |
| 2,181,439 | 11/1939 | Roman | 106/130 |
| 2,286,963 | 6/1942 | Houser et al. | 106/130 |
| 2,308,185 | 1/1943 | Lindsay et al. | 106/130 |
| 2,885,374 | 5/1959 | Sweeny | 106/130 |
| 3,329,509 | 7/1967 | Paris | 106/130 |
| 3,408,214 | 10/1968 | Mentzer | 106/130 |
| 4,076,846 | 2/1978 | Nakatsuka et al. | 426/62 |
| 4,113,673 | 9/1978 | Hirota et al. | 106/130 |
| 4,673,438 | 6/1987 | Wittwer et al. | 106/126 |

FOREIGN PATENT DOCUMENTS 2214920 9/1989 United Kingdom ............ 106/130

OTHER PUBLICATIONS

Hawley, *Condensed Chemical Dictionary*, 8th ed., Van Nostrand Reinhold Co., 1174, p. 949.

*Primary Examiner*—David Brunsman
*Attorney, Agent, or Firm*—Burns, Doane, Swecker & Mathis

[57] ABSTRACT

Disclosed are blendpolymers prepared by suspending at least one protein-containing material and at least one polysaccharide-containing material in at least one solvent, by heating the suspension up to 50° C. until at least 50% of the protein-containing and polysaccharide-containing materials are dissolved, then cooling the mixture down to room temperature and evaporating the solvent. These blendpolymers can be used to manufacture moulded objects, in particular, articles of daily use, preferably bio-compatible articles, such as containers, capsules, foils or films.

20 Claims, No Drawings

BLENDPOLYMERS

BACKGROUND OF THE INVENTION

This application is a continuation of application Ser. No. 07/710,556, filed Jun. 5, 1991, now abandoned, which is a continuation of application Ser. No. 07/286,950, filed Jan. 13, 1989, now abandoned; the content of which is hereby incorporated by reference.

The present invention relates to certain blendpolymers, to processes for their preparation, to their use for the preparation of molded articles, as well as to molded articles which are prepared using such blendpolymers.

Gelatin is a useful biopolymer, which has found several technical applications, e.g., in the food industry, in photography, in the packaging industry and in pharmacology. Processing is an important provision for its application; i.e., processing must be simple and cheap and should allow for simultaneous preparation of different products. Of special interest are those processing methods which allow for mixing gelatin with other components. Therewith one can prepare materials with new characteristics, although the main element is still gelatin. In order to melt gelatin, the gelatin must normally be heated to temperatures above 150° C., usually between 170° C. and 190° C. At these high temperatures, however, many possible additives will be destroyed by the influence of heat. Heating requires a considerable supply of energy, which, of course, is connected with high costs. However, gelatin can also be dissolved in water. The evaporation of water of an aqueous gelatin solution also requires a considerable supply of energy, and is not cheap.

SUMMARY OF THE INVENTION

The invention, among other things, is directed to two new methods for mixing gelatin with different components to provide novel blendpolymers. These materials are especially suitable for preparing films, capsules, foils, containers and other bio-compatible objects.

A primary object of the invention is to mix two polymeric components (e.g., gelatin and starch) in the presence of a third component, which third component has the ability to chemically bind the two polymers to each other, e.g., with hydrogen bridges. Polymers such as starch and gelatin already possess groups with which they may interact with each other in principle. However, starch and gelatin are too rigid and are not sufficiently chemically homogeneous to effectively interact chemically. The intermediate component serves as an adjuvant between the two polymers, in that it functions as an intermediate bridge. Such adjuvants include those components which form simple hydrogen bridges, such as, e.g., urea, glycerin, propylene oxide, ethylene oxide and other polyvalent alcohols, ethylene oxide, polyethylene oxides, polyvinyl alcohols, or amines or amino acids (e.g., glycine) as well as aldehydes, such as formaldehyde, paraformaldehyde and glutaraldehyde, or acids such as formic acid, phosphoric acid and sulfuric acid.

Generally, therefore, the invention is directed to homogeneous blendpolymers. The blendpolymers are obtained by (i) suspending at least one protein-containing material and at least one polysaccharide-containing material in at least one solvent, preferably water; (ii) heating the suspension to a temperature of up to 50° C. for a period sufficient to dissolve at least 50% of the amount of protein-containing material; (iii) adding an adjuvant and at least one biologically active material; and then (iv) cooling the mixture to room temperature and evaporating the solvent.

DETAILED DESCRIPTION OF THE PREFERRED EMBODIMENTS

As noted above, the invention is directed to certain homogeneous blendpolymers. The polymers are prepared by (i) suspending at least one protein-containing material and at least one polysaccharide-containing material in at least one solvent, preferably water. Then, (ii) the suspension is heated to a temperature of up to 50° C. for a period sufficient to dissolve at least 50% of the amount of protein-containing material; and (iii) an adjuvant and at least one biologically active material are added. Thereafter, (iv) the mixture is cooled to room temperature and the solvent is evaporated.

Prior to cooling to room temperature, at least one pigment and/or at least one inorganic salt, such as $ZnCl_2$ or $LiCl_2$, can be added.

The adjuvant is preferably an at least bifunctional, hydrogen bridge-forming compound, such as, e.g., a polyvalent alcohol, preferably ethylene glycol, propylene glycol, urea, ethylene oxide, polyethylene oxides, polyvinyl alcohols, amines, amino acid, preferably glycine aldehydes, preferably formaldehyde, paraformaldehyde, glutaraldehyde, carboxylic acids, preferably formic acids, phosphoric acid, sulfuric acid, pyrophosphate, glycerin or one of its mono-, di- or triesters.

The biologically active material is preferably a biopolymer, preferably enzymes, bacterias, nucleic acids, cells, mithochondrias, plasmides or medicaments.

The protein-containing material is preferably a natural protein-containing material, preferably a flour, a cell extract of animal or vegetable origin, gelatin, elastin or keratin.

The polysaccharide-containing material is preferably selected from the group of starch, amylose, heparin, chitins, chondroitin sulfates and polyglycanes.

The solvent can be selected from the group of water, dioxane, dimethylsulfoxide, formamide or one of its substituted and/or alcylated derivatives, for example methylformamide or dimethylformamide.

According to the present invention, it is preferred that the protein-containing material and the polysaccharide-containing material are present in an amount from 0.5 to 70% by weight, especially 2.5 to 40% by weight, based on the total weight of the solution.

The adjuvant is preferably present in an amount of from 10 to 300% by weight, preferably 30 to 100% by weight, based on the weight of the polysaccharide-containing material.

The pigment, and/or the biologically active material and/or the inorganic salt described above can be present in an amount of from 0.001 to 60% by weight, preferably 1 to 10% by weight, based on the total weight of the solution.

Blendpolymers according to the present invention can be used for the preparation of molded articles, and are particularly useful with processing methods used for processing of polymer melts; particularly mold pressing and film casting. Molded articles according to the invention are particularly useful as a commodity, preferably a bio-compatible commodity, especially as a container, a capsule, a foil or a film.

As another aspect of the invention there is a process for the preparation of blendpolymers by means of (i) dissolving at least one protein-containing material and at least one polysaccharide-containing material in very small amounts of water, (i.e., as little water as possible), (ii) dissolving at least one surfactant in at least one organic solvent, (iii) mixing the two solutions, and (iv) transforming the mixture into a microemulsion gel, wherein the water and/or the organic solvent is evaporated from the gel. In this process, at least one additive can be added before gel formation, preferably at least one pigment, and/or at least one medicament, and/or at least one biologically active material, particularly a biopolymer, preferably enzymes, bacterias, nucleic acids, cells, mithochondrias, plasmides, and/or at least one inorganic salt, for example $ZnCl_2$, $LiCl_2$, and/or at least one co-surfactant.

In the process described above, the protein-containing material can be a natural protein-containing material, particularly a flour, a cell extract of animal or vegetable origin, gelatin, elastin or keratin.

The surfactant can be selected from the surfactant AOT, sodium-1,2-bis(2-ethylhexyloxycarbonyl)-1-ethanesulfonate, benzalconium chloride, CTAB (cethyltrimethyl-ammonium bromide), surfactants based on other quaternary ammonium salts, surfactants based on ethylene glycol, surfactants of natural origin, such as phospholipides, lecithines, phospholecithines, phosphodilcolines, synthetic surfactants having a basic glycerin nucleus, and surfactants having the structure of esters of fatty acids, such as sorbitan-tristearate or polyoxyethylene sorbitan oleat (Polisorbato 80).

In the above process, the organic solvent can be a natural organic solvent, such as squalene, essential oils, terpenes, vegetable oils, miglyol, esters of natural fatty acids, such as for example palmitic acid, stearic acid, etc., perfluorated hydrocarbons and hydrocarbons such as octane, isooctane, pentane, hexane, cyclohexane.

Blendpolymers prepared according to the process described above can be used for the preparation of molded articles, and preferably with those processing methods used in the processing of polymer melts, especially mold pressing and film casting. Such molded articles can be a commodity, preferably a biocompatible commodity, especially a container, a capsule, a foil or a film.

The idea of preparing a blendpolymer which includes a starch and gelatin in the presence of an adjuvant is not described in the literature. It is known that glycerin added to gelatin, does result in an improvement of the processing of the polymer. Mixtures of starch and gelatin are also known. For example, the effect that the addition of gelatin has upon the gel temperature of starch has been examined (J. Djakovic et al., Technol. Mesa 1985, 148–153). A gelatin-starch-sponge has been proposed for medical purposes (Prusyczynski et al., Polim. Med. (1977, 7, 9–17). Other authors have examined the effect of the gelatin Bloom Number on the physical properties of lactose-starch tablets (Georgakopoulos P. P. and Malamataris S., Pharm. Ind. 1976, 38, 728–732). Co-acervates of gelatin and chemically modified starch have been prepared for use as the inner walls of capsules (T. Hayashi and others, Japan. Kokai, 1976, 10, 181). The coacervation of starch and gelatin in the presence of chloral hydrate was examined by H. Y. Chung and M. M. MacMasters (Starke, 18, 1377–82, 1966). But, these studies were limited to solutions and not to the properties of the solid polymers. The influence that starch and lactose have on the release velocity of medicaments from gelatin capsules has also been studied (J. E. Davies, and J. T. Fell, J. Pharm. Pharmacol. 1973, 25, 431–52). Reports also exist concerning starch-extended gelatin products (Szymanski C. D. and G. J. Heimstetter, DE-OS 2 335 509, 1974 U.S. Appl. 272,395, Jul. 17, 1972). Finally, other studies have included the influence of starch on the disintegration of Hart-gelatin-capsules (P. De Beukelaer et al., Drug Dev. Ind. Pharm. 1985, 11, 431) and the films for food industry packages, (Mitsubishi Acetate Co., Ltd., Jpn, Kokai Tokyo Koho JP 60 76, 336 (85 76, 336).

The peculiarity and advantage of the present invention is that the polymer mass may be processed in a very simple way, i.e., by all the usual methods which are used for polymer melts or high viscose masses, including injection molding, calendaring, film casting and extrusion.

An advantage of the present invention is that during the formation of the preferred gelatin polymers, various special components may be added including salts, pigments, heavy metals, fillers, enzymes and bacteria cells, so that materials for quite special purposes, e.g., for biotechnology, may be prepared.

In summary, the invention relates to a new, fast and cheap method for the processing of preferably gelatin, especially for the preparation of biocompatible polymer films and membranes or capsules for pharmaceutical applications.

The preferred gelatin may be mixed in a very simple way with various compounds, which allows for controlling the characteristics of the end products.

Also, enzymes and bacteria may be incorporated in the preferred gelatin polymers.

Below there is described two methods for processing gelatin which are denoted as "first method" and "second method." In addition, examples illustrating these methods are also included.

EXAMPLES

First Method

This method is directed to the preparation of gelatin films of microemulsion gels. A method for preparing gels from water-in-oil microemulsions (or inverse micelle) is described in the above-mentioned references. The method may be summarized as follows: a certain concentration (e.g., 150 mM) of a surfactant which is capable of forming inverse micelles (e.g., aerosol-TO, abbreviated AOT), is dissolved in a hydrocarbon (e.g., isooctane). A concentrated gelatin solution in water (e.g., 10% v:v of a 40% gelatin solution in water) is then added and the mixture is heated to about 50° C. When the mixture is cooled below +30° C., the whole system becomes a gel. These microemulsion gels are characterized using different physical methods, and intensive investigations are in operation in order to clarify the structure of these new materials, and to explore the use range in different domains of pharmacy and physics.

The closest art is described in Swiss Patent Application No. 4983/84-9 and European Patent Application No. 85 904 955.3.

It has surprisingly been found that not only water, but also the solvent (e.g., isooctane), may be removed quantitatively from the gel preparations. The resultant polymer preparations, especially films, consist mainly of gelatin and AOT.

The method may be described by the following four steps:

1.1) Gel formation

First a microemulsion gel is prepared. Suitable solvents include: low boiling paraffins, such as pentane, hexane, cyclohexane; or butane which is liquified under high pressure; or chlorinated hydrocarbons or their mixtures.

1.2) Additives

The components are added either before the formation of the gel or after the gel has been formed. This step is already described in the literature. However, a difference exists in that special components are added, which are used in gelatin films for special applications. Such components are: inorganic salts, such as $ZnCl_2$, LiCl; or organic components such as glycerine and its mono- or di-or triesters; or formamide, methylformamide, and further nitrogen-containing low molecular weight compounds; or biopolymers such as polysaccharides, e.g., heparin, chondroitin sulfates, starch, chitin, cellulose. Other components are synthetic polymers, such as polyisobutylene, polystyrene, and others, which are directly soluble in the oily phase, as well as polymers, such a polyvinyl alcohol, which may be solubilized in the aqueous phase. Stone-powder and riess may also act as additives. Also, enzymes, bacteria, and cell particles, such as mithocondria, may be added. The proportion of these added components may be between 0.001 and 60 percent by weight, especially between 1 and 10 percent by weight.

1.3 Molding

In the third step of the method the prepared gel is processed. In the case of the preparation of foils, the gel material is poured onto a plate. From the earlier literature it appears that there is no recognition that the gels could be processed directly in order to prepare foils, capsules and other objects, which may then be processed in the following step 1.4) into mechanically stable and cheap piece goods. The thickness of the film should be between 0.01 mm and 5 cm, especially between 1 and 5 mm.

1.4 Drying

This operation involves removing the organic solvent from the gel material. Most simply, this can be done by evaporation at room temperature. The evaporation may be accelerated with a warm air device, by heating the form in an oven. The manner depends on the volatility of the solvent. With gels from butane, pentane and hexane, room temperature evaporation is complete within a few hours.

After evaporation of the solvent, films or products result. Chemical analysis has shown that they include gelatin and surfactant (water evaporates together with the organic solvent). An X-ray analysis of the films shows that the material is amorphous.

The obtained films were also tested as membranes for the separation of biomaterial. For example, a test was run to determine whether a film, obtained with 150 mM AOT and 10% gelatin, would pass peptides which were dissolved in chloroform (5 mM concentration of the peptide). It was noted that after three hours 17% Z-phenyl-alanyl-methylester and 24% BOC-tyrosine had passed.

The permeability of the films for gases, such as helium and nitrogen, was also tested (from a gel with 10% gelatin 150 mM AOT, 14% water and isooctane). It has been noted that the material shows a certain selectivity since the permeability of helium was 1.1 and nitrogen was 0.2 $cc/cm^2.cm.s.bar.10^7$.

Example 1.1

At room temperature 10 ml of a 150 mM AOT isooctane solution was added to a 1.4 ml of an aqueous solution containing 1 g gelatin (Blum n.250). This suspension is heated to 50° C., whereby it became clear. A gel formed when the mixture was cooled to room temperature. The gel was then poured onto a metallic plate. After about 5 hours a solid film formed, which was hard and transparent.

Example 1.2

This test was carried out as above, but the aqueous solution contained gelatin, $ZnCl_2$ and 20 mM overall concentration. The resulting gel was not transparent. The film which resulted was hard and transparent.

Example 1.3

This test was carried out as above, but with 20 mM NaSO rather than $ZnCl_2$. Similar characteristics were achieved in the gel and in the film as described above.

Example 1.4

This test was carried out as above, but Tween 85 was added instead of the salt in a concentration of 1.5 percent by weight. The resulting gel was transparent. The film was hard but soluble in water.

Second Method: Blendpolymers of gelatin and starch

The second method involves making blendpolymers, preferably from gelatin, which need no surfactant and no micro-emulsion solution. For example, gelatin and starch are mixed directly, preferably with the aid of an adjuvant, and the result is a blendpolymer. If needed, further additives may be added to the blendpolymer including pigments or biomolecules.

The method may be described, for example, as follows:

1) Gelatin and starch are mixed together in a container. The relative content of starch may be between 0.5 and 90 % by weight, especially between 20 and 60 % by weight. Water is then added, so that the total weight of gelatin and starch is between 0.5 and 70 % of the total weight, especially between 2.5 and 40 %. The suspension is heated under stirring in a water bath to a temperature of 50° C., and the heating continues until the gelatin has dissolved.

2) Glycerin is then added, in a weight proportion of from 10% to 300% of the starch proportion, especially 30 to 100%. The solution is heated to 90° C., whereby the solution becomes very viscous. When the temperature is brought slowly to room temperature, then a gel is formed.

The above described first two steps may also be incorporated in a single working step.

3) The solution is very homogenous. When capsules are prepared (see example), scanning electron microscopy (Hitachi S700) shows no sign of heterogeneity. Preliminary investigations with melting point microscopy show that the capsules become soft and shrink at 150° C.

The water content in the final product (e.g., capsules) can easily be determined since the final parts are kept in a vacuum oven at 60° C. and the weight loss can be measured.

The solution obtained is stable. With lyophilization (freeze-drying) one can obtain a white polymer having good mechanical properties and which is smooth, mechanically stable, and not brittle.

Example 2.1: Preparation of Capsules 5 g wheat starch was mixed together with 8 g gelatin in 130 ml water. In the second step (see above) 5 g glycerin was added to the mixture. The temperature of the solution was maintained at 40°-50° C. max., and capsules were prepared therewith. A "molding bar" which was cooled in the freezer to a temperature of −20° C., and which was slightly lubricated with silicon grease, was introduced into the solution. The "molding bar" was then taken out slowly and dried at room temperature. When the material was dry, the capsules were taken off the metallic fingers. The density of the capsules was easily controlled since the concentration of the solution, the temperature and the viscosity of the solution were all controlled. The water content of the dry capsules was 0.4 % by weight.

Example 2.2: Preparation of Films

General Procedures

In the examples below the following procedures were followed.

All substances were mixed cold until the solution showed no more coarse lumps. Then the solution was heated slowly to 90° C. The solution was continuously stirred at this temperature until the solution became homogenous, transparent and viscous.

Then the solution was processed.

Blendpolymers from Starch and Gelatin with the Aid of Various Components

Example 2.2.1: Glycine

A mixture of 3 g wheat starch, 1.8 g gelatin, 1 g glycine and 50 ml water resulted in a homogenous, slightly transparent and slightly brittle polymer.

Example 2.2.2: Urea

A mixture of 3 g wheat starch, 1.8 g gelatin, 0.9 g urea and 50 ml water resulted in a slightly brittle polymer.

Example 2.2.3: Ethylene glycol

A mixture of 3 g wheat starch, 1.8 g gelatin, 50 ml water and 1 g ethylene glycol resulted in a slightly brittle, very homogenous polymer. When more ethylene glycol was added, e.g., 2 g, a very elastic, homogenous polymer resulted.

Example 2.2.4: Polyvinyl alcohol (15000)

A mixture of 3 g wheat starch, 1.8 g gelatin, 50 ml water and 1 g polyvinyl alcohol resulted in a very homogenous, slightly brittle polymer.

Example 2.2.5: Glycerin

A mixture of 2 g wheat starch, 2.8 g gelatin, 45 ml water and 0.9 g glycerin resulted in a homogenous, very elastic polymer.

If one intends to increase the wheat starch proportion and to use less gelatin, the high elasticity of the polymer may be maintained when higher glycerin concentrations are used.

| Example 2.2.6: Blendpolymer with Ketoprofene | |
|---|---|
| Starting material: | |
| wheat starch | 2 gr |
| gelatin bloom 300 | 1.5 gr |
| glycerin | 1.5 gr |
| ketoprofene (Carlo Erba) (Batch AM 16 BO41) | 350 mg/0.5 ml EtOh |

The mixture of 2 gr starch, 1.5 gr gelatin and 1.5 gr glycerin was suspended at room temperature in 60 ml $H_2O$ under stirring. The mixture was continuously stirred and heated to 90° C. The mixture was stirred for 15 minutes at 90° C. The resulting homogenous mixture was thermostated down under heavy stirring to 40° C. As soon as the temperature of the mixture reached 40° C., 350 mg ketoprofene was added (dissolved in 0.5ml EtOH) under heavy stirring. After about 2 minutes the mixture was poured into polystyrene containers to a thickness of 0.2 ml/cm$^2$, and dried in the air at room temperature.

Example 2.2.7: Blendpolymer powder with ketoprofene

The same preparation was used as above, but without glycerin.

The finished film was brittle and powdered together with dry ice in a mortar.

What is claimed is:

1. A homogenous, moldable blendpolymer of gelatin and starch, said blendpolymer obtained by (i) suspending gelatin and starch in water; (ii) heating the resulting suspension to a temperature of up to 50° C. for a period sufficient to dissolve at least 50% of the gelatin, (iii) adding to the heated suspension a hydrogen bridge-forming adjuvant in an amount effective to form an intermediate bridge between the gelatin and starch, and at least one biologically active material, while maintaining the resulting mixture in solution; and (iv) forming the blendpolymer by cooling the mixture to room temperature and evaporating the water.

2. A homogenous, moldable blendpolymer of gelatin and starch according to claim 1 further comprising at least one of a pigment and an inorganic salt, said at least one of a pigment and inorganic salt being added prior to step (iv).

3. A homogenous, moldable blendpolymer of gelatin and starch according to claim 2, comprising adding said at least one inorganic salt wherein said inorganic salt is selected from the group consisting of $ZnCl_2$ and LiCl.

4. A homogenous, moldable blendpolymer of gelatin and starch according to claim 2, wherein said pigment and/or inorganic salt is added in an amount of 0.001 to 60% by weight of the total solution.

5. A homogenous, moldable blendpolymer of gelatin and starch according to claim 2, wherein said pigment and/or inorganic salt is added in an amount of 1 to 10% by weight.

6. A homogenous, moldable blendpolymer of gelatin and starch according to claim 1, said adjuvant being a bifunctional, hydrogen bridge-forming compound selected from urea, ethylene oxides, polyvinyl alcohols, amines, aldehydes, carboxylic acids, phosphoric acids, sulfuric acids, and pyrophosphates.

7. A homogenous, moldable blendpolymer of gelatin and starch according to claim 1, said adjuvant being bifunctional and selected from ethylene glycol, propylene glycol, glycine, formaldehyde, paraformaldehyde, glutaraldehyde, formic acid, and glycerin or mono-, di, or triesters thereof.

8. A homogenous, moldable blendpolymer of gelatin and starch according to claim 1, said biologically active material being selected from enzymes, and nucleic acids.

9. A homogenous, moldable blendpolymer of gelatin and starch according to claim 1, said biologically active material being a biopolymer.

10. A homogenous, moldable blendpolymer of gelatin and starch according to claim 1, wherein the starch is added in an amount of from 0.5 to 70% based on the total weight of the solution.

11. A homogenous, moldable blendpolymer of gelatin and starch according to claim 8, wherein the starch is added in an amount of 2.5 to 40% by weight.

12. A homogenous, moldable blendpolymer of gelatin and starch according to claim 1, wherein the adjuvant is added in an amount of from 10 to 300% by weight based on the weight of the starch.

13. A homogenous, moldable blendpolymer of gelatin and starch according to claim 12, wherein the adjuvant is added in an amount of 30 to 100% by weight.

14. A homogenous, moldable blendpolymer of gelatin and starch according to claim 1, wherein said biologically active material is added in an amount of 0.001 to 60% by weight of the total solution.

15. A homogenous, moldable blendpolymer of gelatin and starch according to claim 14, wherein the biologically active material is added in an amount of 1 to 10% by weight.

16. A homogenous, moldable blendpolymer of gelatin and starch according to claim 1, said adjuvant being a bifunctional, hydrogen bridge-forming compound selected from polyvalent alcohols, polyethylene oxides and amino acids.

17. A homogenous, moldable blendpolymer of gelatin and starch according to claim 1, said biologically active material being selected from bacterias.

18. A homogenous, moldable blendpolymer of gelatin and starch according to claim 1, said biologically active material being selected from medicaments.

19. A homogenous, moldable blendpolymer of gelatin and starch according to claim 1, said bilogically active material being selected from plasmides.

20. A homogenous, moldable blendpolymer of gelatin and starch according to claim 1, said biologically active material being selected from mithochondrias.

* * * * *